United States Patent [19]

Kalotay et al.

[11] Patent Number: 5,359,881
[45] Date of Patent: Nov. 1, 1994

[54] VISCOMETER FOR SANITARY APPLICATIONS

[75] Inventors: Paul Z. Kalotay, Lafayette; Craig B. Van Cleve, Lyons, both of Colo.

[73] Assignee: Micro Motion, Incorporated, Boulder, Colo.

[21] Appl. No.: 140,740

[22] Filed: Oct. 21, 1993

Related U.S. Application Data

[63] Continuation of Ser. No. 856,089, Mar. 20, 1992, abandoned.

[51] Int. Cl.[5] ............................................. G01N 11/02
[52] U.S. Cl. .................................... 73/54.06; 73/54.09
[58] Field of Search ................. 73/54.05, 54.06, 54.09, 73/54.04, 861.38, 54.02, 54.01

[56] References Cited

U.S. PATENT DOCUMENTS

| | | | |
|---|---|---|---|
| 2,948,145 | 8/1960 | Eolkin | 73/54.06 |
| 3,194,057 | 10/1962 | Richard | 73/54.05 |
| 3,465,573 | 9/1969 | Shoemaker | 73/54 |
| 3,468,158 | 9/1969 | Chien | 73/54.05 |
| 4,350,285 | 9/1982 | Holben | 73/54.06 |
| 4,442,704 | 4/1984 | Swearinyen | 73/54.09 |
| 4,750,351 | 6/1988 | Ball | 73/54.04 |
| 4,768,385 | 9/1988 | Cage | 73/561.38 |
| 4,831,885 | 5/1989 | Dahlin | 73/861.38 |
| 4,843,890 | 7/1989 | Samson et al. | 73/861.38 |
| 5,009,109 | 4/1991 | Kalotay et al. | 73/861.38 |
| 5,054,326 | 10/1991 | Mattar | 73/861.38 |

FOREIGN PATENT DOCUMENTS

| | | |
|---|---|---|
| 9114167 | 9/1991 | Australia . |
| 2559907 | 8/1985 | France . |
| 2622375 | 12/1977 | Germany . |

OTHER PUBLICATIONS

Kalotay, et al., On-Line Viscosity Measurement with Coriolis Mass Flow Meters, ISA, 1991, Paper #91-0448, pp. 1029-1039.

Primary Examiner—Hezron E. Williams
Assistant Examiner—Daniel S. Larkin
Attorney, Agent, or Firm—Duft, Graziano & Forest

[57] ABSTRACT

A viscometer for improved sanitary measurement of the viscosity of industrial fluids. The present invention provides a viscometer integral with a flow meter or a viscometer than can be mounted onto an existing flow meter. The viscometer includes two adjacent parallel flow channels having relatively flat inner surfaces. A differential pressure element is mounted between the adjacent flow channels to sense the differential pressure between the fluid flow of the two channels. The differential pressure is input along with the mass flow rate and fluid density to calculate the fluid viscosity.

32 Claims, 7 Drawing Sheets

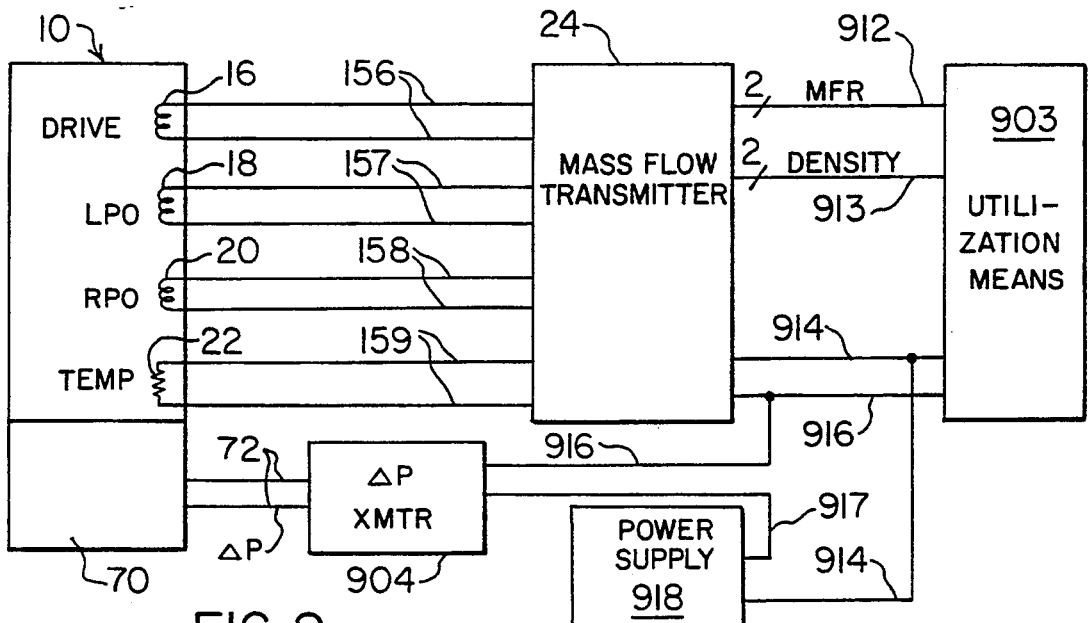
FIG. 9.
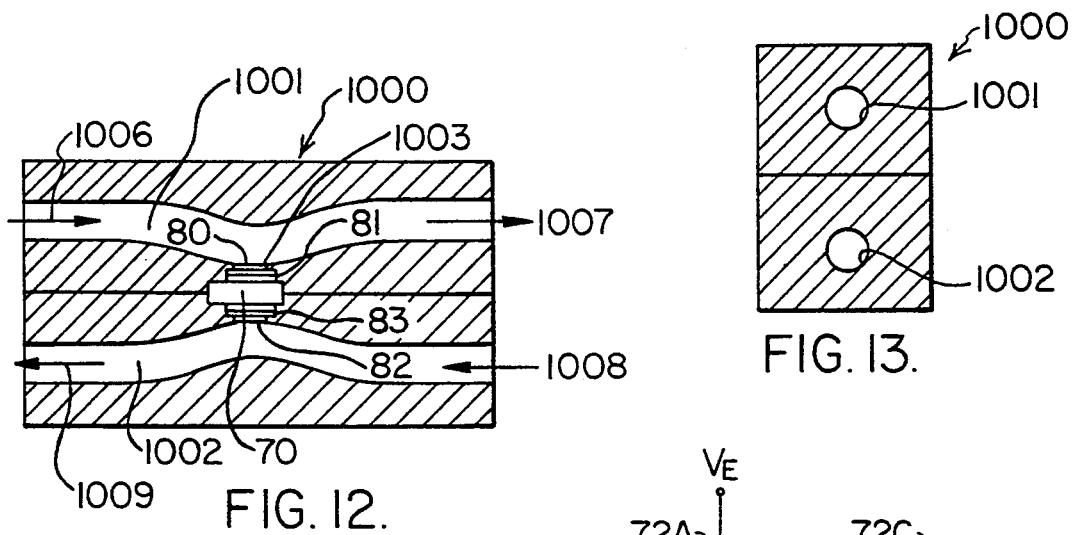
FIG. 12.
FIG. 13.
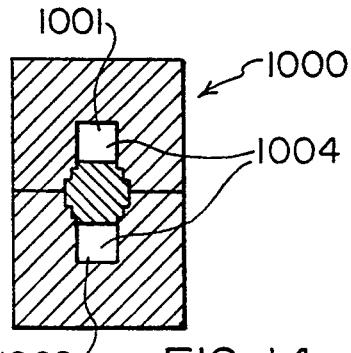
FIG. 14.
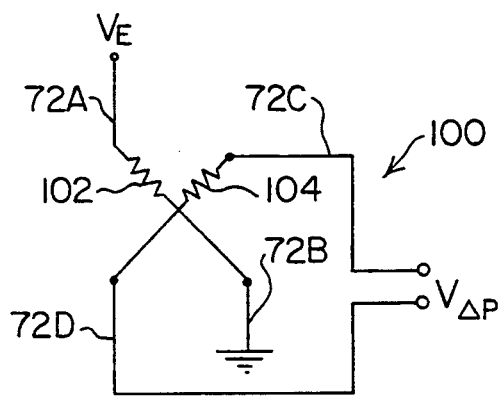
FIG. 6.

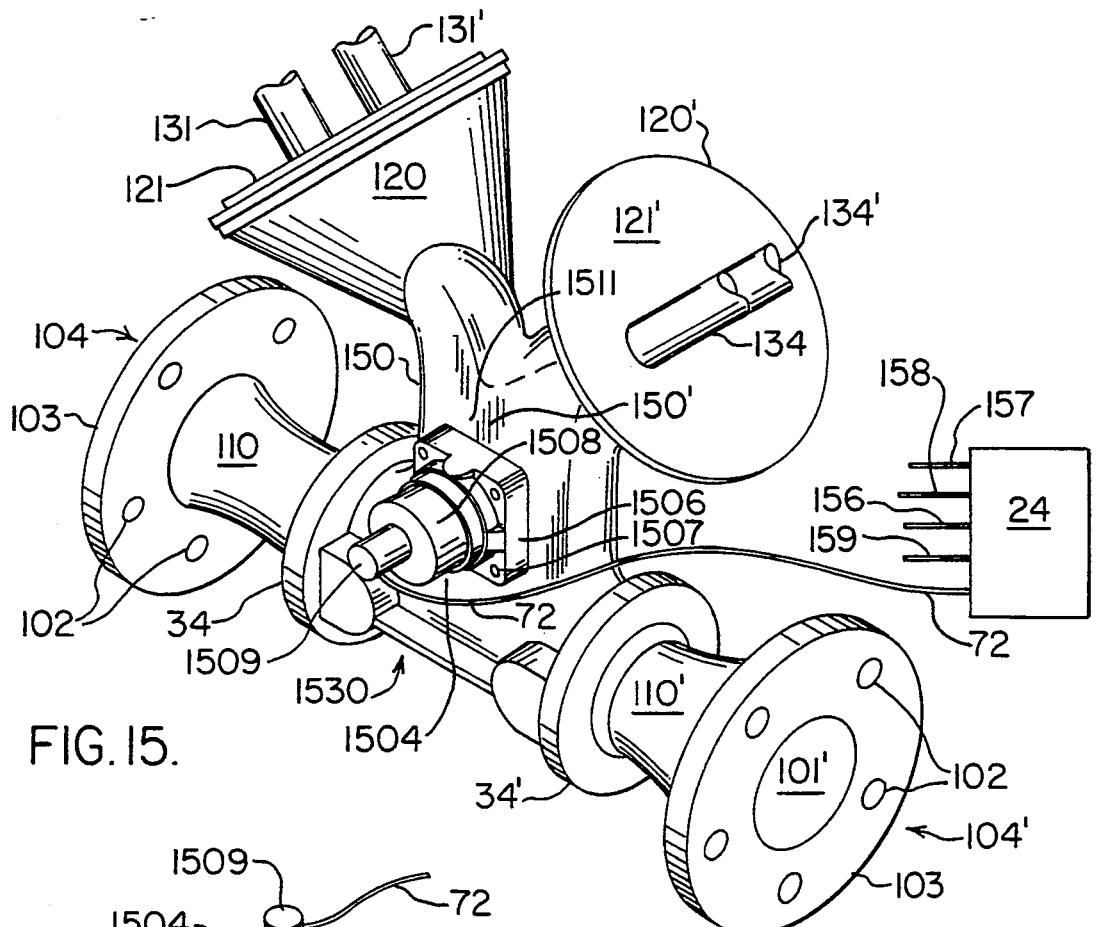
FIG. 15.
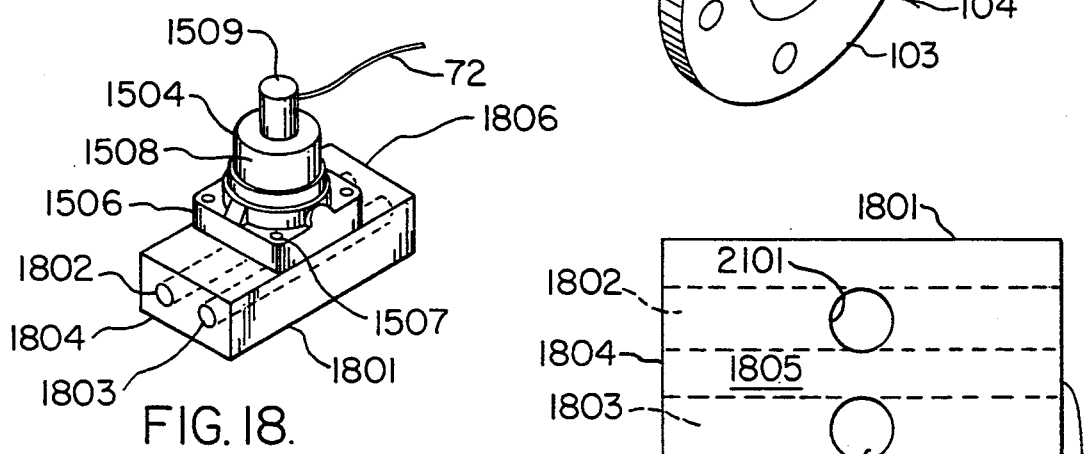
FIG. 18.
FIG. 21.
FIG. 19.

VISCOMETER FOR SANITARY APPLICATIONS

RELATED APPLICATION

This patent application is filed as a continuation of co-pending patent application, bearing Ser. No. 07/856,089, and filed on Mar. 20, 1992,

FIELD OF THE INVENTION

This invention relates to the provision of improved apparatus for and a method of measuring the viscosity of fluids flowing through a flow tube. The invention further relates to the provision of a Coriolis effect viscometer, The invention still further relates to the provision of a viscometer whose internal channels can easily be cleaned so as to make it suitable for applications having stringent sanitary requirements.

PROBLEM

Viscometers are presently used for measuring the viscosity of various types of fluids, e.g. gels, lubricating oils, and other materials that can flow through a tube or conduit. A number of existing methods are employed by these devices for measuring fluid viscosity. One such method is based upon Stoke's Law whereby the rate of movement of a rigid sphere through a fluid is proportional to the viscosity of the fluid. This method involves the travel of a dropped or rolling ball through the fluid.

Another method involves the use of Hagen-Poiseuille's Equation for laminar fluids, i.e. fluids at low Reynolds numbers (less than 2000), and fluids with Newtonian characteristics. The viscosity of the flowing fluid, as determined by Hagen-Poiseuille's Equation, is proportional to the pressure change of the fluid as it flows through a tube as well as to the volumetric flow rate of the fluid. Prior art viscosity measurement devices utilizing Hagen-Poiseuille's Equation typically measure the pressure differential caused by the fluid flow at two distinct locations of the tube through which the fluid flows. The volumetric flow rate of the fluid is either already known or is measured by a flow meter. The viscosity is then determined from the measured differential pressure and the volumetric flow rate which is computed from the mass flow rate and measured density.

These prior art viscometers measure the material viscosity on-line and typically require either flow diversion to a pressure transducer, or the protrusion of a pressure sensor into the flow of the fluid. This can cause various problems including problems with sanitary measurements of the fluid, problems with flow disturbances which can be critical when attempting to measure relatively low pressure drops with high accuracy, problems with the plugging of the diversion tubes which leads to uncontrollable offsets, and problems with the expense and complexity of the instrumentation required for these viscometers.

Many viscometers applications require stringent sanitary conditions of the apparatus passages through which the fluid flows. These sanitary requirements are often difficult to satisfy and are directed towards the finish of the inner surfaces of the viscometers, the interior surface quality, the types of connections used and the ability to clean the viscometer apparatus. It is often an added requirement that the flow tubes of the viscometers must be able to be cleaned in place and without disassembly. As the fluid composition is changed from one material to another, the flow tubes structure must be cleaned to remove the prior material by flushing with steam, solvents, or process fluids. In the prior art viscometers, this often required that the viscometer apparatus be drained and flushed under pressure. Even so, the viscometers may still not meet the most stringent sanitary requirements. Failure to satisfactorily clean the viscometer apparatus may cause health hazards and can contaminate entire batches of materials at great expense to the process operator.

Prior attempts to provide sanitary viscometers that meet these exacting sanitary requirements often used a pressure transducer having a diaphragm that contacted the flowing material by extending beyond the inner surface of the flow tube surface containing the flowing material. These diaphragms are generally ineffective unless they are substantially flat. Due to the circular cross-section of the flow tubes, the use of flat diaphragms protruding beyond the inner surface of the flow tubes, changes the effective shape of the inner cross-section area of the flow tubes. This makes the apparatus difficult to clean without disassembly and creates contamination on the downstream side of the diaphragm. It also alters the velocity profile of the flowing material. This affects the pressure of the fluid and the accuracy of the viscosity measurement.

In summary, the prior art viscosity measurement devices are relatively complex and often require additional piping and sensors. A problem also exists in that many of these devices are unsanitary and cannot be easily cleaned. They also use sensors that protrude into the inner chambers containing the flowing material and thus are not capable of on-line measurements without disturbing the flow of fluids through a flow tube.

SOLUTION

These and other problems are solved by the present invention which provides an improved viscometer for the on-line viscosity measurement of a fluid flowing through a tube or conduit.

The present invention provides a viscometer that does not disturb the fluid flow in the flow tube even at relatively low pressure. The present invention also does not require a diversion of the flow of the measured fluid.

The present invention provides improved sanitary conditions of the measured fluid since the apparatus embodying the invention can easily be cleaned, This is accomplished by the provision of a pressure sensor that does not protrude into the inner chambers containing the flowing fluid, This reduces turbulence and increases the accuracy of the viscosity measurements.

The present invention provides a relatively simple device not requiring complicated apparatus or piping of the measured fluid.

The present invention is useable as an add-on device or can be made integral with installed flow meters.

The particular features of the present invention are evident from the ensuing description of the invention and from the drawing.

SUMMARY OF THE INVENTION

The present invention provides improved apparatus for and method of measuring the viscosity of a flowing material. In one possible preferred exemplary embodiment, the viscometer is integral with a Coriolis effect mass flow meter. The flow meter includes a manifold having two separable castings each having a flow channel formed therein. An inlet flow channel in one casting assumes a substantially flattened rectangular shape as the flow channel curves through the casting. This provides a (relatively) flat inner surface of sufficient dimensions to accommodate a ΔP sensor at a mid point region of the casting. The second casting has an exit flow channel similar to the inlet flow channel and having a similar flat inner surface. Two parallel flow tubes are mounted onto the manifold and connected to the flow channels of the castings. A driving coil is mounted on the flow tubes to oscillate the flow tubes. Sensing coils are positioned relative to the flow tubes to respond to their movement caused by the combination of the vibratory excitation of the flow tubes and the fluid flowing through the flow tubes. Output signals of the sensors are processed to determine the mass flow rate of the fluid passing through the oscillating flow tubes. The difference in time (Δt) between one sensing coil crossing a predefined plane and another sensing coil crossing the same predefined plane is related to the fluid mass flow rate. A temperature sensor is also mounted on the flow tubes to measure the temperature of the flow tubes.

A differential pressure transducer is positioned between the two castings with diaphragms of the differential pressure transducer being positioned substantially flush with the flat inner surfaces of the flow channels of each casting. The transducer diaphragms sense the differential pressure of the fluid created as it flows from the inlet channel of one casting, through the two flow tubes, to the exit channel of the second casting.

A signal corresponding to this sensed differential pressure is transmitted to a process controller along with signals representing the mass flow rate and temperature of the measured material. The pressure transducer output signals are transmitted, in one preferred embodiment, by a multi-drop communication network that allows bi-directional communication between the transducers and the process controller. The density of the fluid is determined from information generated by the mass flow meter. The mass flow rate, density and differential pressure information are then used to determine the viscosity of the fluid according to an equation based on the Hagen-Poiseuille's Equation.

In another possible exemplary embodiment, an adaptor viscometer structure is provided which can be connected to existing flow meters or other flow devices. The body of the adaptor viscometer structure has two parallel adjacent flow channels. The flow channels are constructed so they have a round cross-sectional area at each end of the adapter structure and a rectangular cross-sectional area at the midpoint of the adapter structure. This rectangular portion of each channel has a flat interior surface in which is formed a hole that extends to the flat interior surface of the other channel. A differential pressure transducer is mounted in the hole area between the flow channels so that the diaphragms of the element are substantially flush with the flat inner surface of each flow channel. The diaphragms transfer the pressure of the fluid flowing through each channel to the differential pressure element. A signal representing the detected differential pressure is transmitted to process control apparatus which also receives the mass flow rate and density of the fluid from the flow meter apparatus to which it is connected. The viscosity of the flowing material is then calculated using these variables.

In another possible exemplary embodiment of the invention, a viscometer structure is provided that is somewhat similar to that of the first embodiment except that the differential transducer is externally mounted to a flat surface on the flow meter casting. A first hole is formed in a flat portion of the casting containing the inlet channel and a second hole is formed in the portion of the casting containing the outlet channel. Each hole extends from the flat surface to an inner flat surface of the two channels. The channels have a flat interior surface near the vicinity of the holes. The holes comprise an opening in the casting and represent an inner surface of each flow channel. The two diaphragms of the external pressure transducer are positioned at a spaced-apart distance from each other so as to match the distance of the holes on the exterior flat surface of the casting. The remainder of each channel may be essentially circular except for the portion of each channel to which is connected the vibrating flow tubes.

The external pressure transducer and its diaphragms are mounted by any suitable means so that the diaphragms cover the holes and are flush with the inner surfaces of the two flow channels. This ensures that the diaphragms do not protrude beyond the flat inner surfaces of the flow channels. The diaphragms thereby present a continuous smooth surface to the flowing material. The transducer has output conductors which transmit a signal representing the differential pressure between the inlet channel and the outlet channel of the casting. This signal is transmitted to the same process control circuitry as previously described for the embodiment in which the pressure transducer is internal to the flow tube casting.

The embodiment utilizing the externally mounted pressure transducer is advantageous in many installations over the first embodiment using an internally mounted transducer. The externally mounted transducer is preferable since the transducer can be easily repaired or replaced in the event of a malfunction. This avoids the need of a complete disassembly of the flow tube casting as is the case for the embodiment in which the differential pressure transducer is internal to the flow tube castings.

In still another possible exemplary embodiment, an adapter viscometer structure is provided which can be connected to existing flow meters or other flow devices. The body of the adapter viscometer structure has two internal parallel flow channels having circular cross-sectional areas at their ends and a rectangular cross-sectional area at their middle portion. This middle portion of each channel has a hole formed in the body. The hole comprises the interior surface of each flow channel. A differential pressure transducer is mounted over the two holes with the transducer having two diaphragms spaced apart by a distance corresponding to the distance between the two holes. The pressure sensing diaphragms of the mounted transducer cover the holes and they are flush with the flat inner surface of each flow channel. The diaphragms do not protrude beyond the flat inner surface and therefore do not interfere with the flow of the measured fluid. The diaphragms transfer the pressure of the fluid flowing through each channel to the differential pressure element. A signal representing this detected differential pressure is transmitted to the previously described process control apparatus which also receives mass flow rate, density, and other information required so that the viscosity of the flowing material may be calculated using these variables.

These and other features of the present invention will be evident from a reading of the detailed description of a preferred embodiment taken in conjunctions with the drawings.

BRIEF DESCRIPTION OF THE DRAWING

FIG. 3 is a perspective view of a portion of the casting of the present invention;

FIG. 6 is a schematic of the circuitry of the differential pressure element of FIG. 4;

FIG. 9 is a schematic of another alternative embodiment of the present invention;

FIG. 12 is a cross-sectional view of the alternative embodiment taken along line 12—12 of FIG. 10;

FIG. 13 is a cross-sectional view taken along line 13—13 of FIG. 11;

FIG. 14 is a cross-sectional view taken along line 14—14 of FIG. 11;

FIG. 15 is a perspective view of another alternative structural embodiment of the invention;

FIG. 18 is a view of another possible embodiment of the invention;

FIG. 19 is a cross-section view taken along line 19—19 of FIG. 18;

FIG. 21 is a top view of block 1801 of FIG. 18 with differential pressure transducer 1504 removed.

DETAILED DESCRIPTION

Figure 1:
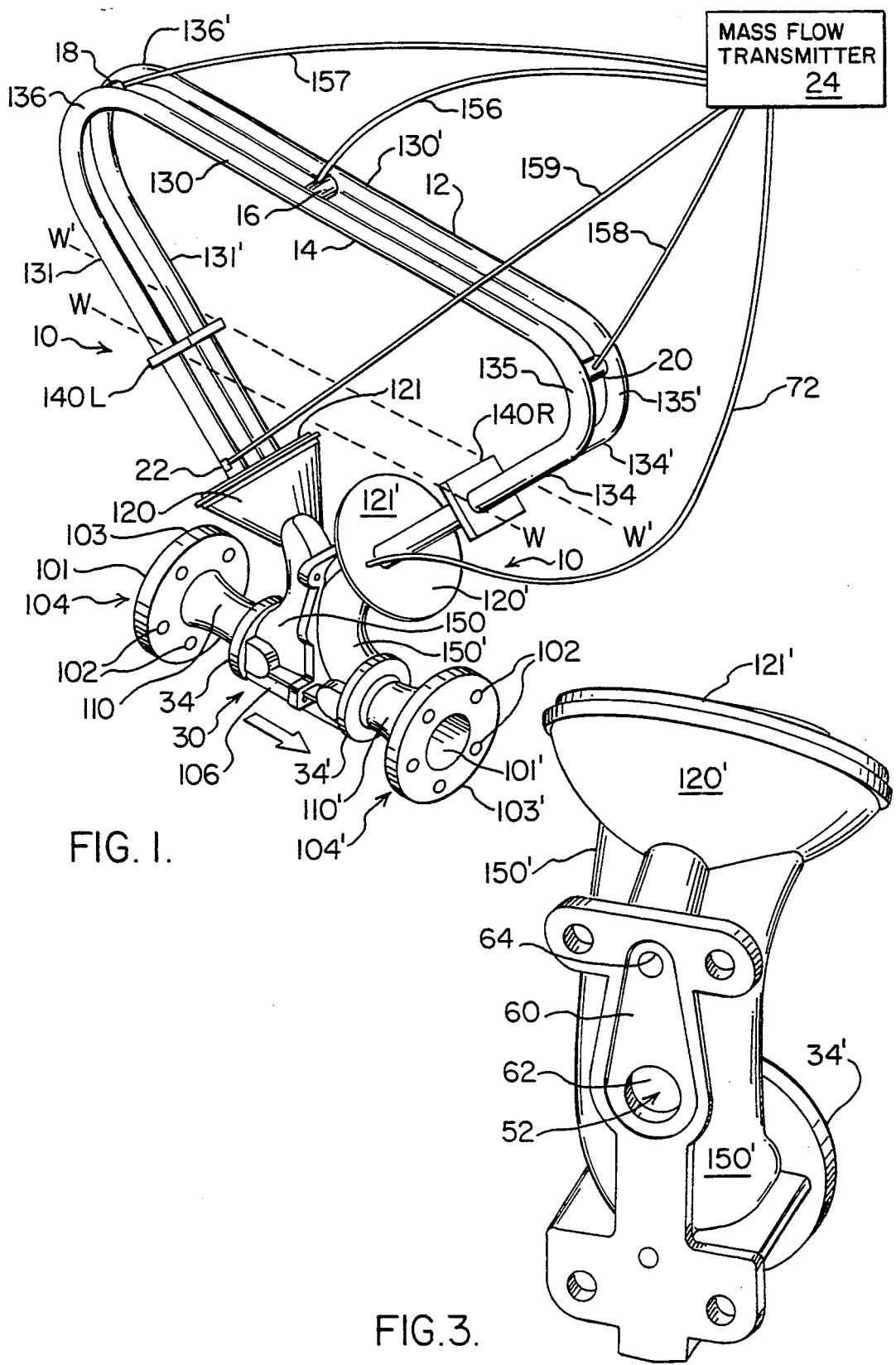
FIG. 1 is a perspective view of one possible preferred exemplary embodiment of the invention integrally combined with a mass flow meter.

The viscometer of the present invention provides a viscosity measurement without disturbing the flow profile of the flowing material. This is important, not only because maintaining the integrity of the flowing material is often vital, but also because disturbances in the flow can alter other measurements in the flow tube and cause cavitation and other undesirable flow characteristics.

The flowing material is referenced herein as a fluid, but it is to be understood that the present invention may have application with other materials, including gases, slurries and the like.

One preferred embodiment of the present invention is a viscometer mounted internal to a Coriolis effect mass flow meter. Coriolis effect flow meters and their operation, are well known, and are disclosed in U.S. Pat. Nos. 4,187,721; 4,491,025; and 4,843,890; all assigned to the assignee of the present invention. Generally, Coriolis effect mass flow meters have one or two parallel flow conduits connected to a manifold body. Both flow conduits are oscillated by a driver to create a rotational frame of reference. As fluid flows through the oscillating conduits, the resulting Coriolis forces cause differences between the vibratory motion of the two flow tubes. One way to measure these differences is to measure the $\Delta t$ between one point on a flow tube crossing a predetermined plane and another point on the tube crossing the same plane. This $\Delta t$ is proportional to the mass of the fluid flowing through the conduits.

One such Coriolis effect mass flow meter 10 is illustrated in FIG. I as having two cantilever mounted flow tubes 12, 14 that are selected and mounted to a manifold body 30 so as to have substantially identical spring constants and moments of inertia about their respective bending axes W-W and W'—W'. A drive coil and magnet 16 are mounted at a midpoint region between the top portion 130 and 130' of flow tubes 12, 14 to oscillate flow tubes 12, 14 about axes W-W and W'—W'. Left sensor 18 and right sensor 20 are mounted near the respective ends of the top portion 130, 130' of flow tubes 12, 14 to sense the movement of flow tubes 12, 14. This sensing may be done either by measuring the movement of the ends 135,136 of the flow tubes through their zero crossings or by measuring the velocity of movement of the flow tubes. Flow tubes 12 and 14 have left side legs 131 and 131' and right side legs 134 and 134'. The side legs converge toward each other at manifold elements 120 and 120'. Brace bars 140R and 140L serve to define the axes W and W' about which each flow tube oscillates when driver 16 is energized over path 156.

Temperature detector 22 is mounted on the side leg 131 of the flow tube 14 to measure the flow tube's temperature and the approximate temperature of the flowing fluid. This temperature information is used to determine changes in the spring constant of the flow tubes. Drive coil 16, sensors 18,20 and temperature detector 22 are connected to mass flow transmitter 24 by paths 156, 157 and 158. Mass flow transmitter 24 may include a microprocessor which processes the signals received from sensors 18, 20 and 22 to determine the mass flow rate of the fluid flowing through flow meter 10 as well as other measurements, such as density and temperature. Mass flow transmitter 24 applies a drive signal over path 156 to drive coil 16 to oscillate tubes 12 and 14 at their natural frequency.

Figure 2:
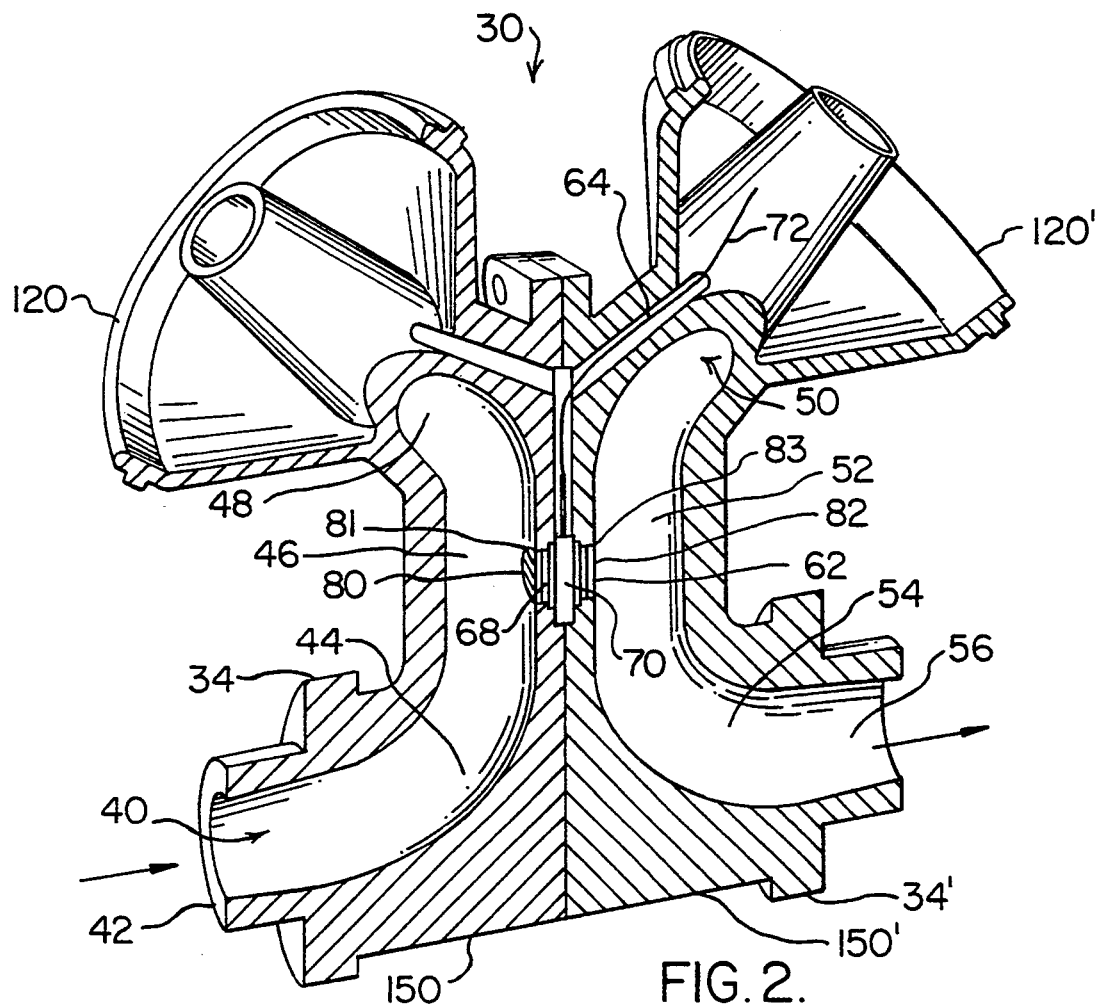
FIG. 2 is a vertical cross-sectional view of the flow meter of FIG. 1.

Manifold body 30 is formed of two separable castings 150, 150' as illustrated in FIGS. 2 and 3. Flow meter casting 30 is attachable to a supply conduit and exit conduit (not shown), by flanges 103, 103'. Manifold body 30 diverts the material flow from the supply conduit into flow tubes 12, 14 and then back into the conduit.

When meter casting 30 having flanges 103 and 103' having holes 102 is connected via inlet end 104 and outlet end 104' to a conduit system (not shown), carrying the process material being measured, the material enters the casting 30 through an inlet orifice 101 in flange 103 of inlet end 104 of manifold 30 and is connected by a channel 40 (FIG. 2) having a gradually changing cross-section in casting 150 to flow tubes 12, 14. The material is divided and routed by block 120 to the left legs 131 and 131' of flow tubes 14 and 12, respectively. The material then flows through tubes elements 130,130' and through the right side legs 134 and 134' and is recombined into a single stream within flow tube mounting block 120'. The fluid is thereafter routed to a channel 50 in exit casting 150' and then to exit manifold element 110'. Within the exit casting 150' the material flows through a channel 50 passageway having a similar gradually changing cross-section to channel 40 of inlet casting 150. Exit end 104' is connected by flange 103' having bolt holes 102' to the conduit system (not shown).

Castings 150, 150' are substantially identical and are secured together to form the manifold body casting 30. Casting 150, (FIG. 2), includes an internal flow channel 40 having a substantially circular cross-section at inlet 42. The circular cross-sectional shape of flow channel 40 near its curved portion 44 begins to flatten until it is substantially rectangular at its mid-portion region 46. Flow channel 40 then splits at its portion 48 into two separate flow channels for connection with side legs 131 and 131' of flow tubes 12,14. The flattening of the cross-sectional shape of flow channel 40 at mid-portion 46 accomplishes two functions. First, the flowing fluid is substantially laminar at the separation of the flow channel into two paths. Second, the inner (right) side of mid-portion 46 is substantially flat.

Casting 150' is substantially identical to casting 150 so that side legs 134 and 134' of flow tubes 12, 14 converge into a single flow channel 50, which has a substantially rectangular cross-sectional shape at its mid-portion 52. The shape of flow channel 50 begins to become circular at its curved region 54 and assumes a circular cross-sectional shape at its outlet 56.

Casting 150', as shown in FIG. 3, includes cavity 60 formed adjacent its mid-portion 52 and has a hole 62 extending through to its mid-portion 52. Wire channel 64 extends from the upper portion of cavity 60 upward through to the upper portion of the exterior of casting 150' via element 120'. This channel 64 receives conductors 72 of differential pressure transducer 70 as subsequently described.

Casting 150 (FIG. 4) includes cavity 61 similar to cavity 60 of casting 150'. Hole 68 extends through casting 150 in its mid-point portion 46. Castings 150, 150' are assembled together and fastened by suitable means in a well-known fashion.

Figure 4:
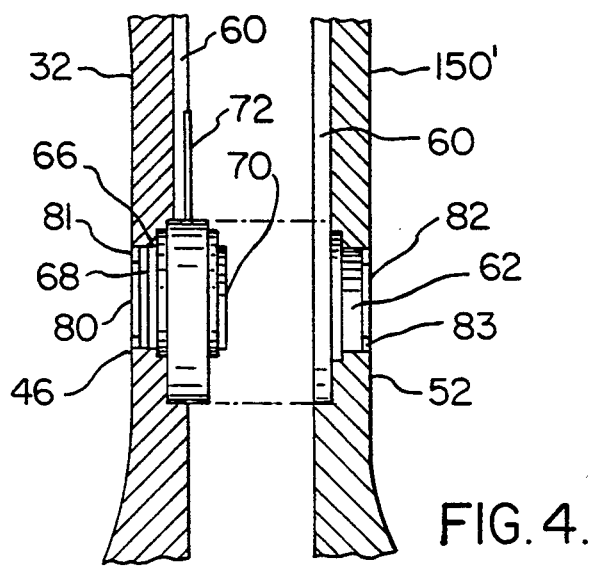
FIG. 4 is a detailed view of the internal mounting of the differential pressure element of the embodiment of FIG. 1.

As shown on FIGS. 2 and 4, differential pressure transducer 70 is positioned in holes 62,68 of cavities 60,61 of the assembled castings 150,150'. Differential pressure element 70, discussed in greater detail below, includes a cable 72 extending upward through wire channel 64 (FIGS. 2 and 3) and further extending to mass flow transmitter 24. Stainless steel diaphragms 80,82 of pressure element 70 are positioned in holes 62,68 (FIG. 4) to be substantially flush with the flat surfaces 46,52 of flow channels 40,50 (FIG. 2) of castings 150, 150'. Molded seals 81,83 provide a tight fit between diaphragms 80,82 and castings 150,150' to ensure that there is no leakage of the material around the diaphragms 80,82 of differential pressure element 70 and the walls 46,52 of castings 150,150' and so that there are no traps or dead spaces to produce turbulence at this region.

Figure 5:
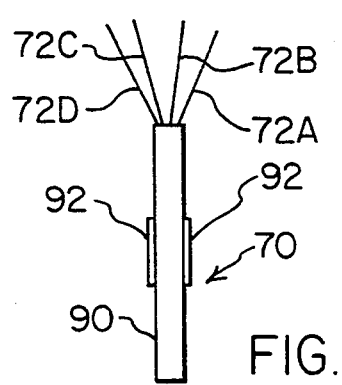
FIG. 5 is a detailed view of the substrate of the differential pressure element 70 of FIG. 4.

The differential pressure element 70 includes a space formed between each stainless steel diaphragm 80,82 and the active pressure portions 92 (FIG. 5) of pressure element 70. These spaces are filled with silicon oil or other suitable liquid to transfer the pressure applied against stainless steel diaphragms 80,82 to element 92 of differential pressure element 70. This maintains the sensor in close proximity with the process fluid. Differential pressure element 70, in the preferred embodiment, is a semiconductor pressure sensor, such as MOTOROLA differential pressure element ZD MPX2200D M8822. As shown in FIG. 5, differential pressure element 70 includes silicon substrate 90 having resistive deposits 92 formed thereon in a resistive pattern. Differential pressure is created between the fluid flowing through flow channel 40 of casting 150 and the fluid flowing through flow channel 50 of casting 150'. This differential pressure causes a distortion of substrate 90 to create a resistive change in differential pressure element 70. Distortions of the substrate 90 due to differential pressure change the resistances of the resistive patterns, The circuitry of differential pressure element 70 of FIG. 5 is shown in FIG. 6. This circuitry includes a resistor 102 and a resistor 104. Resistor 102 is connected at its ends to conductors 72A and 72D which supply a source of energizing potential $V_E$ and ground. Resistor 104 is connected at its ends to conductors 72B and 72C which extend to a pair of output terminals across which appears an output voltage $V_{\Delta P}$ which represents the differential pressure across pressure element 70. Resistor 104 is positioned within the electric field generated by resistor 102 as it is energized by potential $V_E$. The strength of the electrical field induced into resistor 104 varies in accordance with the differential pressure exerted on the diaphragms on the two sides of element 70. In other words, resistor 104 applies an output voltage to conductors 72b and 72c that is proportional to the differential pressure across the two sides of element 70. This differential output voltage is indicative of the differential pressure seen by the two sides of pressure element 70. In accordance with the present invention, this output voltage $V_{\Delta P}$ can be used by associated circuit elements and apparatus to compute the viscosity of the material flowing through the two tubes with which differential pressure element 70 cooperates.

Viscometer 10 (FIG. 1) is adapted to be installed in a supply conduit, such as an industrial pipeline. The fluid flow from the supply conduit (not shown) is conducted via inlet 42 (FIG. 2) to input flow channel 40 within manifold casting 150. As the fluid flow nears mid-portion 46 of channel 40, flow channel 40 has a substantially rectangular cross-sectional shape. The flow at this region contacts diaphragm 80 which is substantially flush with the flat surface 46 of flow channel 40, This contact of the fluid against diaphragm 80 applies pressure against the left side of differential pressure element 70. The material flow continues through casting 150 and element 120 as flow channel 40 diverges into flow tubes 12,14.

The return flow from tubes 12 and 14 enters element 120' of manifold casting 150'. Channel 50 receives this return flow. Channel 50 converges and has a substantially rectangular cross-sectional shape at its mid-point portion 52. The return fluid flow passes over diaphragm 82 which receives the return fluid pressure onto the right side of differential pressure element 70. The fluid flow continues through return channel 50 which assumes a circular cross-sectional shape at its exit portion 54 and reenters the supply conduit at its outlet 56 (FIG. 2).

The mass flow rate of the fluid is determined by measuring the time delay between the flow tube movements relative to a predefined plane as the flow tubes are oscillated by driving coil 16. This measurement is made by sensors 18,20.

Signals from temperature detector 22 and sensors 18,20 are transmitted to mass flow transmitter 24 (FIG. 1 ) which processes the signals to determine the mass flow rate, the density and the tube temperature. Signals from differential pressure element 70 are transmitted to processor over path 72. These signals are used by mass flow transmitter 24 along with the determined mass flow rate and density of the fluid to calculate the viscosity of the fluid.

Figure 7:
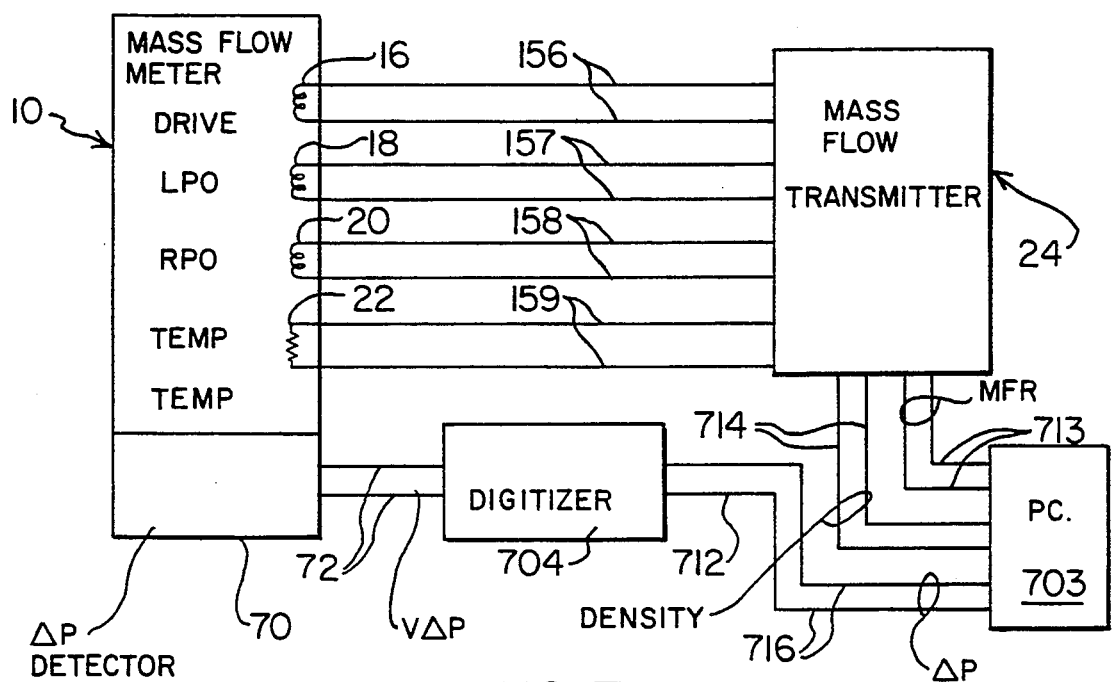
FIG. 7 is a schematic of one possible preferred exemplary embodiment of the invention.

The following describe several embodiments by means of which the output voltage $V_{\Delta P}$ of differential pressure element 70 may be used to generate viscosity information for the material flowing through the flow tube apparatus associated with the differential pressure detector 70. A first embodiment is shown in FIG. 7 which comprises a mass flow meter 10, a differential pressure detector 70, mass flow transmitter 24, a personal computer 703 and a digitizer 704 together with conductors interconnecting these various elements.

Mass flow transmitter 24 applies a drive signal 156 to mass flow meter 10. It also receives from mass flow meter 10 the signal 157 from the left sensor 18, signal 158 from the right sensor 20 and signal 159 from temperature detector 22. From these signals, mass flow transmitter 24 computes the mass flow rate, the density and other pertinent information pertaining to the material flowing through the tubes of mass flow meter 10. The details of mass flow transmitter 24 are well-known in the art and may comprise any of a number of off-the-shelf products manufactured by Micro Motion, Inc., of Boulder, Colorado. Such products have Micro Motion model numbers RFT 9712 and RFT 9739. The differential pressure signal $V_{\Delta P}$ is generated by element 70 and is applied over path 72 to digitizer 704 which digitizes the analog signal 72 and applies it out over path 712 to personal computer 703. The personal computer also receives the mass flow rate information from mass flow transmitter 24 over path 713 and the density information over path 714. From this information, the personal computer 703 performs the necessary computations to solve the following equation to compute the viscosity of the material flowing within the flow tubes associated with differential pressure element 70. This equation is based on the Hagen-Poiseuille Equation:

$$\mu = K \frac{\Delta P \rho}{m} \tag{1}$$

$\mu$ = Viscosity of the fluid $K$ = A constant determined for the individual meter $\Delta P$ = Differential pressure $\rho$ = density of the fluid $m$ = mass flow rate of the fluid This equation is solved when a user at the personal computer determines and enters the value for the element K in the above equation.

Figure 8:
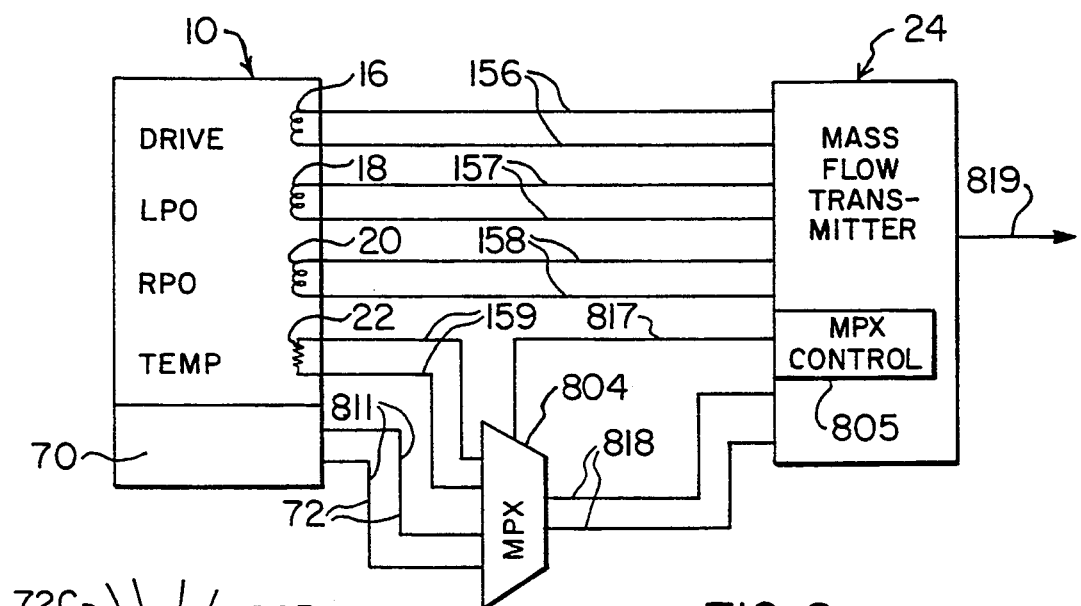
FIG. 8 is a schematic of an alternative embodiment of the present invention.

FIG. 8 shows a second possible alternative arrangement for computing viscosity information. FIG. 8 discloses a mass flow meter 10, shown on FIG. 1, together with a differential pressure detecting transducer 70, a mass flow transmitter 24, a multiplexer 804, together with conductors interconnecting these various elements. Mass flow transmitter 24 applies a drive signal to path 156 and receives from mass flow meter 10 a left sensor signal 157 and a right sensor signal 156. A temperature signal is applied over path 159 to one set of inputs of multiplexer 804 while the ΔP pressure differential signal 72 of element 70 is applied to the other input of multiplexer 804. The operable state of multiplexer 817 is controlled by the MPX controller 805 of mass flow transmitter 24 over path 817. The output of multiplexer 804 is applied over path 818 to mass flow transmitter 24.

The operative position of multiplexer 804 is switched at a required rate by mass flow transmitter 24 over path 817 so that the output 818 of the multiplexer is alternatively connected to temperature signal 159 at one instant of time and, at other times, is connected to the differential pressure signal on path 72. With these two signals alternatively being supplied as inputs to the mass flow transmitter 24, path 818 at one time supplies temperature information to mass flow transmitter 24 and, at other times, supplies differential pressure information. Mass flow transmitter 24 responds in the conventional well-known manner when the conductor pair 818 supplies temperature information to compute mass flow rate, density and other information pertaining to the flowing material within the mass flow meter 10.

At other times, when mass flow transmitter 24 receives differential pressure information from path 818, it uses this information and the aforementioned equation to derive viscosity information for the material flowing within the tubes of mass flow meter 10. This viscosity, and other information if desired, is applied over path 819 to a suitable utilization means (not shown). For the embodiment of FIG. 8, mass flow transmitter 24 is programmed to provide the required constant information representing the term K in the above-discussed equation. Mass flow transmitter may be a Micro Motion, Inc., model 9739 device.

An embodiment representing yet another possible embodiment is disclosed in FIG. 9. This embodiment comprises mass flow rate meter 10, differential pressure transducer 70, a mass flow rate transmitter 24, utilization means 903, differential pressure transmitter 904, power supply 918, and conductors interconnecting these various elements. This embodiment uses the well-known 4–20 Ma (milliamp) analog signaling combined with frequency shift keying signaling (FSK) to transmit information between certain of these elements as subsequently described. This system uses what is known as HART ® (highway addressable remote transmitter) signaling.

Drive coil 16 receives a drive signal over path 156 from element 902. Signals from sensors 18 and 20 and temperature detector 22 are transmitted over paths 157, 158 and 159 to mass flow transmitter 24. Mass flow transmitter 24, which may be a Micro Motion, Inc., model 9739 device, includes a microprocessor which receives these signals and generates mass flow rate information and density information pertaining to the material in the flow tubes. This information is applied over conductors 912 and 913 to utilization means 903 which may comprise a display unit or may comprise a process control system which uses the information generated by mass flow transmitter 24 to control an industrial process. These signals are transmitted over an industry standard 4–20 Ma type signaling system.

The differential pressure transducer 70 generates a signal representing the differential pressure and applies it over path 72 to transmitter 904 which digitizes this information and applies a signal representing the measured differential pressure in FSK digital form over conductors 916 and 917. The ΔP transmitter 904 and mass flow transmitter 24 both use 4-20 Ma analog signaling and frequency shift signaling to communicate with each other. Specifically, ΔP transmitter 904 transmits the digitized ΔP signal via FSK signaling over paths 916 and 917 to the mass flow transmitter 24. Mass flow transmitter 24 receives this &P information and uses it in the formula $$\mu = K \frac{\Delta P \rho}{m} \quad (2)$$

$\mu$ = Viscosity of the fluid $K$ = A constant determined for the individual meter $\Delta P$ = Differential pressure $\rho$ = density of the fluid $m$ = mass flow rate of the fluid to compute the viscosity of the fluid flowing in the tubes 12 and 14. Having computed this information, mass flow transmitter 24 transmits the generated viscosity information over paths 914 and 916 in the form of a 4-20 mA signal to the utilization means 903.

The use of the 4-20 mA signaling together with the FSK signaling is done in accordance with the well-known multi-drop multiplex network technique using the highway addressable remote transducer (HART protocol developed by Rosemount Incorporated and described in Rosemount Smart Family Product Data Sheet 2695 entitled The HART Smart Communication Protocol). This protocol allows the use of bi-directional digital communication over the 4-20 mA process control signal loops without disrupting the process control signal. This is done by means of the well-known frequency shift keying technique based upon the Bell 202A communications standard.

The HART protocol is further described in a document by Romilly Bowden dated January 1991 and copyrighted in 1991 by Rosemount AG. This document, which is herein incorporated by reference, describes in detail the details of a system embodying the HART protocol. It is to be understood that the HART protocol, FSK signaling, as well as the 4-20 mA signaling protocol are all well-known in the art and do not comprise any portion of the present invention and are therefore not described further herein.

Regardless of the process control circuitry used, the measured viscosity is calculated in the same fashion using a modification of the Hagen-Poiseuille's Equation. According to the Hagen-Poiseuille's Equation, $$Q = \frac{\pi \Delta P a^4}{8 \mu l} \quad (3)$$

$Q$ = Volumetric flow rate $\Delta P$ = Differential pressure between two flow locations $a$ = Flow tube cross-sectional area $\mu$ = Viscosity of the fluid $l$ = Distance between the two flow locations This equation is rearranged to determine the viscosity of the fluid according to:

$$\mu = K \frac{\Delta P \rho}{m} \quad (4)$$

-continued $\mu$ = Viscosity of the fluid $K$ = A constant determined for the individual meter $\Delta P$ = Differential pressure $\rho$ = density of the fluid $m$ = mass flow rate of the fluid Therefore, by measuring the differential pressure within flow meter 10 and utilizing the mass flow rate measurement and density measurements from the flow meter, the fluid viscosity can be determined.

A large number of measured fluids exhibit Newtonian characteristics so the above calculations are accurate. However, for non-Newtonian fluids, the above process can be used with only a narrow segment of the operating range of the viscometer. Other solutions for measuring non-Newtonian fluids include characterizing the particular fluid being measured or defining the governing shear rate-viscosity equation through external computations or in a specifically designed electronics package.

An alternative embodiment of the invention is illustrated in FIGS. 10-14. This embodiment comprises an adaptor 1000 which is designed to be retro-fitted to existing flow meters, or used in conjunction with other flow meters or used in situations where the flow rate is already known. Adaptor 1000 includes two parallel flow channels 1001,1002. Cavity 1003 (FIG. 11) is formed between channels 1001,1002 for receiving differential pressure element 70, described above, see FIG. 11. Flow channels 1001,1002 both have circular cross-sectional shapes at their inlet and outlet portions (FIG. 13) and a rectangular mid-portion 1004 (FIG. 14) in the vicinity of cavity 1003. The cross-sectional area of the rectangular portion 1004 of channels 1001,1002 is identical to the inlet and outlet cross-sectional areas. This provides a laminar flow with unchanged velocity across the diaphragms 80,82 of differential pressure element 70. Stainless steel diaphragms 80,82 are flush within the flat surfaces of flow channels 1001,1002 (FIG. 12) their mid-portion regions. Seals 81,83 seal diaphragms 80,82 and differential pressure element 70 from leakage as well as eliminating traps and turbulence of the fluid flow.

Inlet portion 1006 (FIG. 12) of flow channel 1001 is adapted to be fitted onto a supply conduit, or if the supply conduit is of a large diameter, then onto a smaller diameter branch tapped into the supply conduit. Outlet portion 1007 of flow channel 1001 is mounted to an inlet of an existing flow meter or else onto an adaptor to channel the flow back to flow channel 1002. Inlet portion 1008 of flow channel 1002 is mounted onto the outlet portion of the existing flow meter. Outlet portion 1009 of flow channel 1002 is mounted onto the supply conduit or branch (not shown).

The process control circuitry for adaptor assembly 300 is similar to one of the process control circuitry embodiments discussed above. The operation of adaptor assembly 1000 is similar to the above-described integral viscometer. The fluid flow extends through flow channel 1001 across diaphragm 80 into an existing flow meter or flow device. The flow then extends out of the flow meter or flow device and into channel 1002 and across diaphragm 82, as indicated by the arrows (FIG. 12). Differential pressure element 70 senses the differential pressure between channels 1001,1002 and transmits a signal corresponding to this measured differential pressure via one of the described process control systems or by other known process control systems. For instance, the differential pressure signal may be utilized through HART multi-drop networking along with another signal, such as a temperature signal. The particular process control system utilized with adaptor assembly 1000 depends upon the existing flow device that adaptor assembly is installed upon. Since the differential pressure signal generated by the adaptor assembly is in the form of a DC voltage, a variety of process control systems known in the art can be used. In any event, either a volumetric flow rate or a mass flow rate with a density measurement is determined, and supplied to the appropriate process control system. This enables the viscosity to be determined, based upon the above-described calculation.

Figure 16:
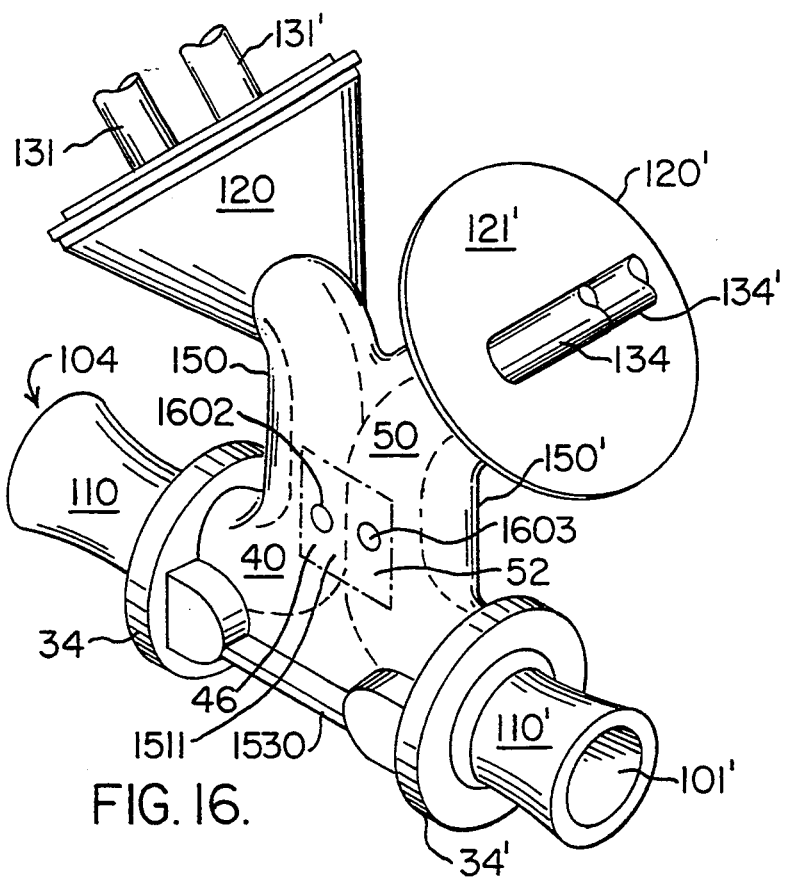
FIG. 16 is a view of the embodiment of FIG. 15 with the differential pressure transducer removed.
Figure 10:
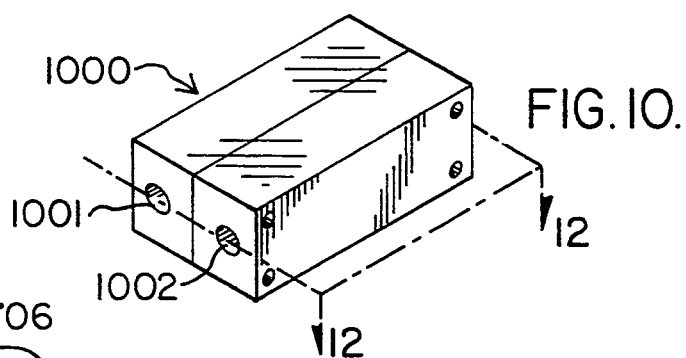
FIG. 10 is a perspective view of an alternative embodiment of the invention.
Figure 17:
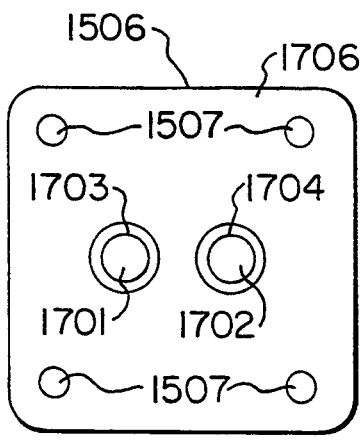
FIG. 17 is a bottom view of the differential pressure transducer of FIG. 15.
Figure 11:
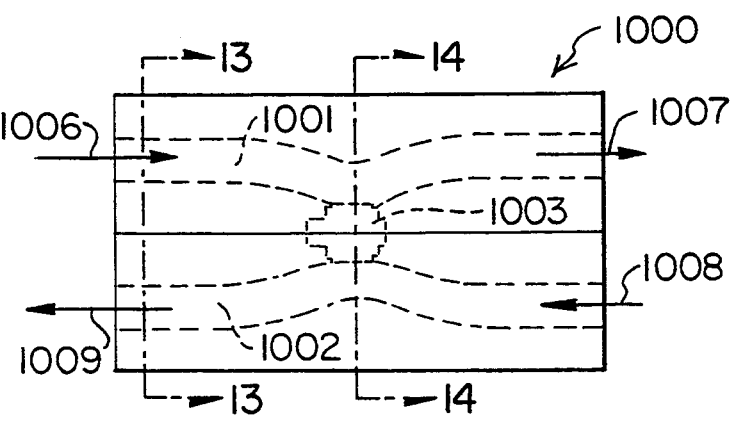
FIG. 11 is a top view of the element of FIG. 10.

FIGS. 15, 16 and 17, disclose an alternative embodiment of the invention in which a differential pressure transducer 1504 is mounted externally to a casting similar to that of FIG. 1. On FIG. 1, differential pressure transducer 70 (FIG. 2) is positioned between an input channel 40 and an exit channel 50 internal to casting 30. Casting 1530 (FIGS. 15 and 16) is similar to casting 30 of FIG. 1 but is adapted to receive external differential pressure transducer 1504. Casting 1530 includes an inlet 104, a flange 103, holes 102, input manifold 110, flange 34, a left casting portion 150, and manifold element 120 having a surface 121 to which are connected the side legs 131,131' of flow tubes 12,14. The remainder of the flow tubes and driver 16, sensors 18,20, and temperature element 22 are not shown on FIG. 15 since they are identical to that of FIG. 1. The right side portion 150' of casting 1530 has corresponding elements to left portion 150 numbered in a corresponding manner with a prime (') following each such corresponding number i.e., casting portion 150'.

The casting 1530 inlet channel 40 is shown on FIG. 16 and extends from inlet manifold 110, through the left side casting portion 150, to the left manifold element 20 to which are connected the left side legs 131,131' of the flow tubes 12,14. FIG. 16 also shows the exit flow channel 50 which extends from the right manifold element 120', through the right side casting portion 150' to manifold element 110' on the outlet portion of casting 1530. Casting 1530 has a flat front portion 1511 that is common to both casting elements 150 and 150' containing the inlet channel 40 and outlet channel 50. Front casting portion 1511 comprises a flat smooth surface that is adapted to receive a bottom smooth surface of differential pressure transducer 1504. On FIG. 16, flat surface 1511 has holes 1602 and 1603 extending through the casting to inlet channel 40 and exit channel 50.

Holes 1602 and 1603 are spaced apart by a distance that corresponds to the distance between two pressure sensing diaphragms 1701 and 1702 on the bottom surface 1706 (FIG. 17) of base 1506 of differential pressure transducer 1504. FIG. 17 is a bottom view of differential pressure transducer element 1504. The bottom of base 1504 contains the two diaphragms 1701 and 1702 surrounded by seals 1703 and 1704. The diaphragms are adapted to be in alignment with holes 1602 and 1603 of casting surface 1511 when the base 1506 is affixed, by means of holes 1507 and suitable mounting screws, to flat surface 1511 of casting 1530.

On FIG. 15, differential pressure transducer 1504 comprises base 1506, circular element 1508, circular element 1509 together with conductors 1511 which extend to mass flow transmitter 24. Differential pressure transducer 1504 is not shown in detail herein since it is a commercially available element and may comprise the Rosemount Smart Family Model No. 3051C differential pressure transmitter. When transducer 1504 is mounted on casting surface 1511, its diaphragms 1701 and 1702 are in alignment with holes 1602 and 1603 so that diaphragms 1701 and 1702 are flush with the inner surfaces of flow channels 40 and 50. The diaphragms do not protrude into the channels or disturb the flow of the fluid within these channels.

Differential pressure transducer 1504 and its diaphragms 1701 and 1702 monitor the pressures in flow channels 40 and 50 and transmit signals over conductors 72 representing the differential pressure between the two flow channels. These signals are extended over conductors 72 to mass flow transmitter 24 of FIG. 1. Mass flow transmitter 24 operates as described for FIG. 1 and receives signals from the left sensor 18, right sensor 20, and temperature detector 22. Mass flow transmitter 24 also applies drive signals to a drive element 16. Elements 16, 18, 20, and 22 are not shown on FIGS. 16 and 16 since they are identical to the showing of FIG. 1.

Figure 20:
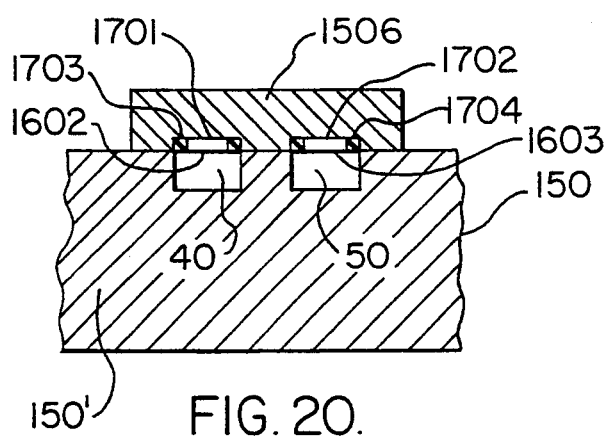
FIG. 20 is a vertical cross-section view of a portion of the flow channels 40 and 50 of casting 1530 of FIG. 16.
Figure 22:
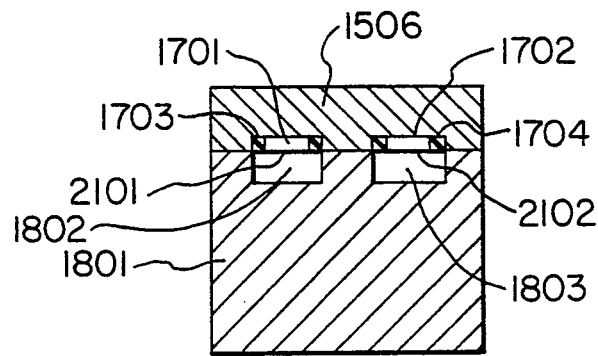
FIG. 22 is a cross-section view taken along line 22—22 of FIG. 21.

On FIGS. 15 and 16, flow channel 40 is circular in cross-section in its inlet portion at input manifold 110. However, inlet channel 40 changes its configuration so that it becomes essentially a rectangular cross-section configuration in its mid portion 46 (FIG. 16) in the vicinity of hole 1602. This is shown in FIG. 20 where the rectangular cross-section portion of channel 40 has an upper side that extends through the wall of casting 1530 in the vicinity of hole 1602. Thus, when pressure transducer 1504 is mounted on flat surface 1511 of casting 1530, its diaphragms 1701 and 1702 cover holes 1602 and 1603 so that its the diaphragms are flush with the top surface of inlet channels 40 and 50 (FIG. 20). This enables the pressure of the flowing fluid to be measured without disturbing the fluid flow pattern.

The embodiment of FIG. 15 with its externally mounted differential pressure detector 1530 often may be advantageous over the embodiment of Figure I where the differential pressure detector 70 is internal to casting 30. The externally mounted differential pressure detector 1504 facilitates maintenance when problems occur. In such cases, the differential pressure detector 1504 may be unbolted from casting 1530 and repaired or replaced with a minimum of effort. For the embodiment shown in Figures I and 2, the separate halves 150 and 150' of casting 50 must be separated in order to gain access to the differential pressure detector 70. This is time consuming and expensive as compared to the time required to repair or replace the externally mounted differential pressure detector 1504 of FIG. 15.

Yet another alternative embodiment of the invention is illustrated in FIGS. 18, 19, 21, and 22. This embodiment comprises an externally mounted differential pressure detector 1504 and an adaptor 1801 (FIG. 18) which is designed to be retrofitted to existing flow meters, or used in conjunction with other flow meters or to be used in situations in which the flow rate is already known. Adaptor 1801 includes two parallel flow channels 1802 and 1803. The adaptor also has holes 2101 and 2102 (FIG. 21) on its top surface which comprise one side of the flow channels 1802 and 1803 in the middle portion of the casting as shown in FIG. 19. The diaphragms 1701 and 1702 of differential pressure detector 1504, as described in connection with the embodiment of FIG. 15, cover holes 2101 and 2102 and contact the fluid flowing within each of channels 1802 and 1803.

The flow channels 1802 and 1803 have a circular cross-sectional shape at their inlet and outlet portions (FIG. 18) and a rectangular mid portion cross section 2201 and 2202 (FIG. 22) in the vicinity of holes 2101 and 2102. The cross-sectional area of the rectangular portion of the channel is identical to the inlet and outlet circular cross-sectional areas. This provides a laminar flow with unchanged velocity across the diaphragms 1702 and 1703 of differential pressure detector 1504. The stainless steel diaphragms 1702 and 1703 are flush with the flat top portion of the flow channels as shown in FIG. 19 for diaphragms 1702 and channel 1803. Seals 1703 and 1704 (FIG. 17) seal the diaphragms 1702 and 1703 and the differential pressure element 1504 from leakage.

Inlet portion 1804 of flow channel 1802 and 1803 is adapted to be fitted onto a suitable conduit. Outlet portion 1806 of the flow channel 1803 is adapted to be connected to an inlet of the existing flow meter or else onto an adaptor to channel the flow back to channel 1802. Flow channels 1802 and 1803 are configured in the manner shown on FIG. 19 for channel 1803. The inlet of channels 1802 and 1803 have a circular cross-sectional area (FIG. 18) and an essentially rectangular cross-sectional area 2201 and 2202 (FIG. 22) at its mid portion in the vicinity of holes 2101 and 2102. The outlet portion of the flow channels is circular and may be connected to an existing flow meter or other structure or else may be returned by a suitable connection back to the outlet end of flow channel 1803.

On FIG. 19, the stainless steel diaphragms 1701 and 1702 are mounted on the upper surface of adaptor element 1801 in such a manner that they cover the holes 2101 and 2102 in the flow channels 1802 and 1803 and are flush with the upper interior surface of the essentially flat top inner surface of the flow channels in the vicinity of holes 2101 and 2102.

In summary, a viscometer is provided by the present invention either as an integral viscometer or as an adaptor assembly for use on existing flow meters or flow devices. The viscometer of the present invention in either embodiment provides an on-line measurement of fluid viscosity for stringent sanitary applications. The present invention provides a viscosity signal that is easily adapted onto most process control systems.

It is to be expressly understood that the described preferred embodiments are set forth for explanatory purposes only and are not meant to limit the scope of the claimed inventive concept. Other embodiments and modifications are considered to be within the scope of the claimed invention,

We claim:

1. Apparatus for determining the viscosity of material flowing in a supply conduit, said apparatus comprising:
   a first flow tube means connected to a second flow tube means;
   said first tube means being effective for transporting said material from a first section of said supply conduit to said second flow tube means;
   said second flow tube means being effective for transporting said material to a second section of said supply conduit;
   at least a portion of said first flow tube means and at least a portion of said second flow tube means being positioned adjacent to and integral with one another;
   said portion of first flow tube means and said portion of said second flow tube means each having a separate internal flow channel with each flow channel having a substantially flat inner surface;
   differential pressure sensing means coupled to said internal flow channel of both said first flow tube means and said second flow tube means for measuring the differential pressure generated by said material flow between said first flow tube means and said second flow tube means;
   a pair of pressure sensing diaphragms on said differential pressure sensing means with each of said diaphragms comprising a surface that is substantially flush with said substantially inner flat surfaces of a different one of said internal flow channels so as to provide a smooth surface for material flow in each of said flow tube means; and
   means responsive to said measurement of said differential pressure for determining the viscosity of said material.

2. The apparatus of claim 1 wherein said apparatus further comprises:
   means for determining the mass flow rate of said material in said first and second flow tube means; and
   means for using said mass flow rate measurement in said viscosity determination.

3. The apparatus of claim 1 wherein said apparatus further comprises:
   Coriolis effect flow meter means for determining the mass rate of flow of said material through said first and second flow tube means, said Coriolis flow meter including:
   driving means for oscillating flexible portions of said first and second flow tube means;
   motion sensing means responsive to the motion of said flexible portions of said first and second flow tube means resulting from the Coriolis effect of said flowing material while said flexible portions of said first and second flow tube means are oscillating for generating a signal representing said motion;
   means for determining the mass flow rate of said material in response to said generation of said signal representing said motion;
   means for determining the density of said material in response to said determination of said mass flow rate; and
   means for transmitting signals corresponding to said determined flow rate and said determined density to said viscosity determining means wherein said viscosity is determined using said determined mass flow rate and said determined density and said measurement of said differential pressure.

4. The apparatus of claim 1 wherein said flow channels of said first and second flow tube means are incorporated into an adaptor block;
   a substantially flat exterior surface on one face of said adaptor block;
   said differential pressure sensing means being external to said block and having a substantially flat exterior surface;
   said pair of pressure sensing diaphragms of said sensing means being flush with said substantially flat exterior surface of said sensing means;
   a pair of openings in said substantially flat exterior surface of said adaptor block with each opening extending from said substantially flat exterior surface of said adaptor block into a different one of said flow channels of said adaptor block; and means for affixing said substantially flat exterior surface of said differential pressure sensing means to said substantially flat surface of said block so that said diaphragms of said differential pressure sensing means cover said openings in said block and are flush with said substantially flat inner surface of each of said flow channels of said first and second flow tube means.

5. The apparatus of claim 1 wherein said first and second flow tube means are incorporated into an adaptor block comprising a first separable casting and a second separable casting which are affixed together;

a void in each of said castings configured to form a single larger void when said first and second castings are affixed together;

said differential pressure sensing means being positioned in said larger void between said flow channel of said first flow tube means and said flow channel of said second flow tube means;

said pair of pressure sensing diaphragms positioned on opposite sides of said differential pressure sensing means;

each of said pressure sensing diaphragms being positioned in said first and second castings so as to be flush with said substantially flat inner surface of a different one of said flow channels.

6. The apparatus of claim 1 wherein said apparatus further comprises:

a casting containing said flow channels of both said first flow tube means and said second flow tube means;

a substantially flat area on an exterior surface of said casting;

openings on said substantially flat area extending into said casting to said substantially flat inner surface of each of said flow channels;

a substantially flat surface on said differential pressure sensing means;

said diaphragms of said differential pressure sensing means being positioned on said substantially flat surface of said differential pressure sensing means;

said differential pressure sensing means being affixed to said casting so that said substantially flat surface of said differential pressure sensing means abuts said substantially flat area of said casting so that said diaphragms are substantially flush with said substantially flat inner surface of each of said flow channels.

7. The apparatus of claim 1 wherein said first flow tube means and said second flow tube means transport the entirety of said fluid flowing in said conduit; and wherein said first flow tube means has a constant inner cross-sectional area equal to a constant inner cross-sectional area of said second flow tube means.

8. Apparatus for determining the viscosity of a flowing material, said apparatus comprising:

first flow tube means including a first flow channel for transporting said material;

second flow tube means including a second flow channel serially connected to said first flow tube means for transporting said material;

a portion of said first flow tube means and a portion of said second flow tube means being positioned adjacent and integral to one another;

each of said flow channels having a substantially flat inner surface;

differential pressure sensing means coupled to both said first flow tube means and said second flow tube means for measuring the differential pressure generated by material flow between said first flow tube means and said second flow tube means;

said differential pressure sensing means being coupled to said substantially flat inner surfaces of each of said flow channels so that pressure sensing diaphragms of said sensing means are substantially flush with said substantially flat inner surfaces of said flow channels to provide a smooth surface for said material flow in each of said flow tube means; and means responsive to said measurement of said differential pressure for determining the viscosity of said material.

9. The apparatus of claim 8 wherein said apparatus further comprises:

a casting containing said flow channels of both said first flow tube means and said second flow tube means;

a substantially flat area on an exterior surface of said casting;

openings on said substantially flat area extending into said casting to said substantially flat inner surface of each of said flow channels;

a substantially flat surface on said differential pressure sensing means;

said diaphragms of said differential pressure sensing means being positioned on said substantially flat surface of said differential pressure sensing means;

said differential pressure sensing means being adapted to be affixed to said casting so that said substantially flat surface of said differential pressure sensing means abuts said substantially flat area of said casting so that said diaphragms are substantially flush with said substantially flat inner surface of each of said flow channels.

10. The apparatus of claim 8 wherein said first and second flow tube means are formed in a pair of separable castings which are adapted to be affixed together with said sensing means being positioned in a void in said affixed castings between said first flow tube means and said second flow tube means.

11. The apparatus of claim 8 wherein said apparatus further comprises:

Coriolis flow meter means for determining the mass rate of flow of said material through said first and second flow tube means, said Coriolis flow meter means including:

driving means for oscillating flexible portions of said first and second flow tube means;

position sensing means responsive to the change in position of said flexible portion of said first and second flow tube means resulting from the Coriolis effect of said flowing material while said flexible portions of said first and second flow tube means are oscillating for generating a signal corresponding to said position change;

determining means responsive to said generation of said position change signal for determining the mass flow rate of said material;

means for determining the density of said material in response to said determination of said mass flow rate; and means for transmitting signals corresponding to said determined mass flow rate and said density to said viscosity determining means wherein said viscosity is determined using said measured mass flow rate signal and said density signal and said measured differential pressure signal.

12. The apparatus of claim 8 wherein said differential pressure sensing means comprises a semiconductor differential pressure element means having a first and a second pressure sensing element for sensing said differential pressure.

13. The apparatus of claim 8 wherein said apparatus further comprises means for transmitting a signal from said differential pressure sensing means to said means for determining said viscosity in response to said measured pressure differential; and wherein said transmitting means comprises a bi-directional communication network between said sensing means and said determining means.

14. The apparatus of claim 8 wherein said apparatus further comprises:

means for determining the mass flow rate of said material in said first and second flow tube means;

means for transmitting a signal representing said determined mass flow rate to said means for determining said viscosity;

means for measuring the temperature of said material; and means for transmitting a signal representing said differential pressure and said measured temperature to said viscosity determining means, said means for determining viscosity being effective for using said mass flow rate determination and said measured temperature in said viscosity determination.

15. Apparatus for determining the viscosity of material flowing in a supply conduit, said apparatus comprising:

a Coriolis effect flow meter including a first and a second flow tube means connected in series for measuring the mass flow rate of said material through said supply conduit, said first and second flow tube means being connected to separate sections of said conduit;

said first tube means being effective for transporting said material from a first section of said supply conduit to said second flow tube means;

said second flow tube means being effective for transporting said flowing material to a second section of said supply conduit;

said Coriolis effect flow meter further including:

driving means for oscillating flexible portions of said first and second flow tube means;

motion sensing means responsive to the motion of said flexible portions of said first and second flow tube means caused by the Coriolis effect of said flowing material while said flexible portions of said first and second flow means are oscillating for generating a signal corresponding to said motion;

means for determining the mass flow rate of said material in response to said generation of said signal;

means for determining the density of said material in response to said determination of mass flow rate;

said apparatus further comprising:

an inner wall of a body portion of said first flow tube means and an inner wall of a body portion of said second flow tube means positioned contiguous with each other;

an opening extending from the interior of said body portion of said first flow tube means, through said inner wall of each of said first second flow tube means;

differential pressure sensing means positioned within said opening for measuring the differential pressure generated by material flow between said first flow tube means and said second flow tube means; and means for transmitting signals corresponding to said determined flow rate and said determined density to said viscosity determining means for determining said viscosity using said determined mass flow rate and said determined density and said measurement of said differential pressure.

16. The system of claim 15 wherein said differential pressure sensing means is coupled to a substantially flat inner wall portion of said first flow tube means as well as to a substantially flat inner wall portion of said second flow tube means; and wherein said substantially flat inner wall portions of said first flow tube means and said substantially flat portion of said second flow tube means are parallel and adjacent to each other; and means for mounting said differential pressure sensing means in said opening between said two substantially flat inner wall portions so that diaphragms of said differential pressure sensing means are substantially flush with each of said substantially flat inner wall portions.

17. The system of claim 15 wherein said differential pressure sensing means is mounted in said opening between said first and second flow tube means within an adaptor assembly connected between said sections of said supply conduit and a flow meter to generate information for determining said viscosity of said material flowing through said conduit.

18. The system of claim 15 wherein said first flow tube means comprises a first separable casting;

said second flow tube means comprises a second separable casting;

wherein said first separable casting and said second separable casting are affixed together with said opening containing said differential pressure sensing means comprising a part of said affixed together separable castings; and wherein said flow meter means is integral to both said first casting and said second casting.

19. A method for determining the viscosity of a fluid flowing in a supply conduit, said method comprising the steps of:

transporting said flowing fluid from a first section of said supply conduit through a first flow tube means to a second flow tube means;

transporting said flowing fluid from said second flow tube means to a second section of said supply conduit;

positioning an inner wall of a body casting portion of said first flow tube means and an inner wall of a body casting portion of said second flow tube means contiguous with and substantially parallel to each other;

forming an opening extending from the interior of said body casting portion of said first flow tube means, through said inner wall of said first flow tube means and through inner wall of said second flow tube means, to the interior of said body casting portion of said second flow tube means;

operating differential pressure sensing means positioned within said opening for measuring the differential pressure generated by fluid flowing between said first flow tube means and said second flow tube means; and determining the viscosity of said fluid in response to said measurement of said differential pressure.

20. The method of claim 19 wherein said method further comprises the steps of:
oscillating flexible portions of said first and second flow tube means;
operating motion sensing means responsive to the motion of said flexible portions of said first and second flow tube means caused by the Coriolis effect of said flowing fluid while said flexible portions of said first and second flow tube means are oscillating for generating a signal corresponding to said motion;
determining the mass flow rate of said fluid in response to said generating of said signal;
determining the density of said fluid in response to said determination of mass flow rate; and
determining the viscosity of said fluid in response to said measurement of pressure differential and said determination of said mass flow rate and said density.

21. The method of claim 19 wherein said differential pressure sensing means is coupled to a substantially flat portion of an inner surface of a first flow channel of said first flow tube means as well as to a substantially flat portion of an inner surface of a second flow channel of said second flow tube means;
wherein said substantially flat portion of said first flow channel and said substantially flat portion of said second flow channel are parallel and adjacent to each other; and
said differential pressure sensing means is positioned between and substantially flush with said substantially flat portion of each of said flow channels.

22. The method of claim 21 wherein said differential pressure sensing means is mounted between said first and second flow channels comprising part of an adaptor assembly serially connected between said sections of said supply conduit and a flow meter to generate information for determining said viscosity of said fluid flowing through said flow meter.

23. The method of claim 21 wherein said first flow tube means and said casting of said second flow tube means comprise separable castings; and
wherein said separable castings are affixed together with said differential pressure sensing means being positioned in said opening between said separable castings; and
wherein said flow meter means is integral to both of said castings.

24. A method for determining the viscosity of a material flowing in a supply conduit, said method comprising the steps of:
transporting said flowing material from a first section of said supply conduit through a first flow tube means connected in series with a second flow tube means;
transporting said flowing material from said first flow tube means and through said second flow tube means to a second section of said supply conduit;
a body portion of said first flow tube means and a body portion of said second flow tube means being integral with one another;

said body portion of said first flow tube means and said body portion of said second flow tube means each have a separate internal flow channel with each flow channel having a substantially flat inner surface;
positioning a pair of pressure sensing diaphragms on a pressure sensing means substantially flush with said substantially inner flat surfaces of said flow channels so as to provide a smooth surface for material flow in each of body portions of said first and second flow tube means;
operating said differential pressure sensing means for measuring the differential pressure generated by material flow between said first flow tube means and said second flow tube means; and
determining the viscosity of said material in response to said measurement of said differential pressure.

25. The method of claim 24 wherein said method further comprises the steps of:
determining the mass flow rate of said material; and
using said mass flow rate determination in said viscosity determination.

26. The method of claim 24 wherein said method further comprises the steps of:
oscillating flexible portions of said first and second flow tube means;
operating motion sensing means responsive to the motion of said flexible portions of said first and second flow tube means resulting from the Coriolis effect of said flowing material for generating a signal representing said motion;
determining the mass flow rate of said material in response to said generation of said signal representing said motion;
determining the density of said material in response to said determination of said mass flow rate; and
transmitting signals corresponding to said determined flow rate and said determined density to said viscosity determining means wherein said viscosity is determined using said determined mass flow rate and said determined density and said measurement of said differential pressure.

27. The method of claim 24 wherein said method further comprises the steps of:
determining the mass flow rate of said material;
transmitting a signal representing said determined mass flow rate to said means for determining said viscosity;
measuring the temperature of said material; and
transmitting a signal representing said differential pressure and said measured temperature to said means for determining said viscosity, said means for determining viscosity being effective for using said mass flow rate determination and said measured temperature in said viscosity determination.

28. The method of claim 24 wherein said flow channels of said first and second flow tube means are incorporated into an adaptor block having a substantially flat exterior surface on one face of said adaptor block, and wherein:
said differential pressure sensing means is external to said block and has a substantially flat exterior surface;
said pair of pressure sensing diaphragms of said differential pressure sensing means being flush with said substantially flat exterior surface of said sensing means, said method further comprising the steps of:

forming a pair of openings in said substantially flat exterior surface of said adaptor block with each opening extending from said substantially flat exterior surface of said adaptor block into a different one of said flow channels of said adaptor block; and affixing said substantially flat exterior surface of said differential pressure sensing means to said substantially flat surface of said block so that said diaphragms of said differential pressure sensing means cover said openings in said block and are flush with said substantially flat inner surfaces on said flow channels.

29. The method of claim 24 wherein said flow channels of said first and second flow tube means are incorporated into an adaptor block comprising a first separable casting and a second separable casting which are adapted to be affixed together and wherein;

a void in each of said castings forms a single larger void when said casting are affixed together;

said differential pressure sensing means being positioned in said larger void between said flow channel of said first flow tube means and said flow channel of said second flow tube means;

said pair of diaphragms being positioned on opposite sides of said differential pressure sensing means;

each of said diaphragms being positioned in said casting so as to be flush with said substantially flat inner surface of said flow channel in each of said castings.

30. The method of claim 24 wherein said method further comprises the steps of:

forming a casting containing said flow channels of both said first flow tube means and said second flow tube means;

forming a substantially flat area on an exterior surface of said casting;

forming openings on said substantially flat area extending into said casting to said substantially flat inner surface of each of said flow channels;

forming a substantially flat exterior surface on said pressure sensing means;

said diaphragms of said differential pressure sensing means being positioned on said substantially flat exterior surface of said differential pressure sensing means; and affixing said differential pressure sensing means to said casting so that said substantially fiat exterior surface of said differential pressure sensing means abuts said substantially flat area of said casting whereby said diaphragms are flush with said substantially flat inner surface of each of said flow channels.

31. A method for measuring the viscosity of material flowing serially through a first and a second flow tube, said method comprising the steps of:

positioning a first portion of said flow tube and a second portion of said flow tube contiguous with and substantially parallel to one another, said portions having substantially symmetrical cross-sections;

said portion of first flow tube means and said portions of said second flow tube means each having a separate internal flow channel with each flow channel having a substantially flat inner surface;

said portion of said first flow tube means and portion of said second flow tube means being part of an adaptor assembly adapted to be affixed to a flow meter;

positioning a differential pressure sensing means in an opening extending between the interior of said portion of said portion of said first flow tube means and the interior of said portion of said second flow tube means for measuring the differential pressure of said flowing material between each of said flow tube portions;

said differential pressure sensing means having a pair of pressure sensing diaphragms with each of said diaphragms comprising a surface that is substantially flush with said substantially inner flat surfaces of a different one of said internal flow channels so as to provide a smooth surface for material flow in each of said flow tube means;

transmitting a signal from said differential pressure sensing means to a determining means with said signal representing said measured differential pressure; and operating determining means for determining the viscosity of said flowing material in response to said transmission of said signal.

32. The method of claim 31 wherein said method further comprises the step of:

connecting said first flow tube means and said second flow tube means to a coriolis effect mass flow rate meter for a determination of the mass flow rate of said material; and said step of determining said viscosity is responsive to said step of determination of said mass flow rate.

* * * * *